United States Patent [19]

Takeuchi et al.

[11] 4,238,294

[45] Dec. 9, 1980

[54] PROCESS FOR RECOVERING HEAVY METAL IONS OR HEAVY METAL IONS AND HALOGEN VALUES FROM SOLUTIONS COMPRISING A LOWER ALIPHATIC MONOCARBOXYLIC ACID

[75] Inventors: Hiroshi Takeuchi, Nobeoka; Tetsuya Miyake, Tokyo; Masatoshi Tanouchi, Nobeoka; Tatsushi Saeki, Nobeoka; Kazuki Ban, Nobeoka, all of Japan

[73] Assignee: Asahi Kasei Kogyo Kabushiki Kaisha, Osaka, Japan

[21] Appl. No.: 928,980

[22] Filed: Jul. 28, 1978

[30] Foreign Application Priority Data

Apr. 10, 1978 [JP] Japan .................................. 53/41233

[51] Int. Cl.³ .......................... B01D 3/00; C01G 1/00
[52] U.S. Cl. ...................................... 203/72; 203/41; 203/71; 562/606; 562/608; 75/101 BE; 423/DIG. 14; 423/24; 423/49; 423/54; 423/63; 423/100; 423/139
[58] Field of Search ........... 75/101 BE; 423/DIG. 14, 423/24, 49, 54, 63, 100, 139; 203/71, 72; 252/413

[56] References Cited

U.S. PATENT DOCUMENTS

| 2,304,637 | 12/1942 | Hardy .............................. 75/101 BE |
| 3,880,920 | 4/1975 | Wampfter ............................. 252/413 |
| 4,086,267 | 4/1978 | Bartlett et al. ......................... 203/71 |
| 4,162,991 | 7/1979 | Jones ..................................... 423/139 |

FOREIGN PATENT DOCUMENTS 899288 6/1962 United Kingdom .

*Primary Examiner*—Herbert T. Carter
*Attorney, Agent, or Firm*—Frishauf, Holtz, Goodman & Woodward

[57] ABSTRACT

A process for recovering heavy metal ions or heavy metal ions and halogen values from a solution comprising a lower aliphatic monocarboxylic acid, which comprises the steps of:

(1) contacting a lower aliphatic carboxylic acid solution containing heavy metal ions or heavy metal ions and halogen values with an anion exchange resin, at least 60% of the ion-exchange groups of said anion exchange resin being in the bromide or chloride state, while the water concentration in the lower aliphatic monocarboxylic acid solution has been adjusted to a level lower than 20% by weight, thereby to adsorb the heavy metal ions or the heavy metal ions and the halogen values on the anion exchange resin; and (2) desorbing the adsorbed heavy metal ions or the adsorbed heavy metal ions and the adsorbed halogen values from the anion exchange resin by elution with an eluent. In the present invention, the halogen values remaining in the lower aliphatic monocarboxylic acid solution which has been contacted with the anion exchange resin can be further recovered by contacting the solution with another anion exchange resin or subjecting the solution to distillation.

7 Claims, 5 Drawing Figures

RELATIONSHIP BETWEEN AMOUNT OF HEAVY METAL IONS ADSORBED AND WATER CONCENTRATION

A : HEAVY METAL IONS HAVING HIGH ADSORBABILITY

B : HEAVY METAL IONS HAVING LOW ADSORBABILITY

RELATIONSHIP BETWEEN AMOUNT OF COBALT IONS ADSORBED AND WATER CONCENTRATION

RELATIONSHIP BETWEEN AMOUNT OF MANGANESE IONS ADSORBED AND WATER CONCENTRATION

RELATIONSHIP BETWEEN AMOUNT OF COBALT IONS ADSORBED AND WATER CONCENTRATION

RELATIONSHIP BETWEEN AMOUNT OF MANGANESE IONS ADSORBED AND WATER CONCENTRATION

PROCESS FOR RECOVERING HEAVY METAL IONS OR HEAVY METAL IONS AND HALOGEN VALUES FROM SOLUTIONS COMPRISING A LOWER ALIPHATIC MONOCARBOXYLIC ACID

This invention relates to a process for removing and/or recovering heavy metal ions or heavy metal ions and halogen values from solutions comprising a lower aliphatic monocarboxylic acid. More particularly, the present invention relates to an improved process for removing and/or recovering, by using an anion exchange resin, heavy metal ions or heavy metal ions and halogen values from lower aliphatic monocarboxylic acid solutions containing, dissolved therein, catalyst heavy metal ions, impurities of heavy metal ions formed by corrosion of a reaction apparatus and the like and halogen values used as the reaction promotor.

In the instant specification and claims, the term "halogen values" is intended to include those halogens in the form of halogen ions such as bromine ions and chlorine ions and non-dissociative halogen compounds such as organic bromine compounds and organic chlorine compounds.

Recently, there have been widely practiced on an industrial scale liquid phase oxidation processes in which aliphatic hydrocarbons such as methane, ethane and butane, aliphatic aldehydes such as formaldehyde and acetaldehyde, aromatic aldehydes such as benzaldehyde and tolualdehyde, and aliphatic group-substituted aromatic compounds such as toluene, ethylbenzene, xylenes and mesitylene are oxidized to the corresponding alcohols, aldehydes and carboxylic acids by means of a molecular oxygen-containing gas in a lower aliphatic monocarboxylic acid solvent in the conjoint presence of at least one heavy metal compound as a catalyst and a halogen compound, especially a bromine compound, as a reaction promotor.

In these liquid phase oxidation processes, it is of significant necessity to recover the aliphatic monocarboxylic acid, the heavy metal catalyst and the halogen compound, because they are expensive. For their recovery, there have been proposed various processes and some of the processes are practiced in the art.

For example, Japanese Patent Application Laid-Open Specification No. 123192/1974 discloses a process in which the mother liquor obtained from the reaction mixture of the liquid phase oxidation is subjected to distillation to remove the aliphatic monocarboxylic acid, and the distillation residue containing reaction intermediates, a reaction product, organic impurities, bromine, heavy metal ion impurities and the like is subjected to extraction with water in the presence of a sulfur compound to remove, as the solid extraction residue, impurity heavy metal ions other than cobalt and manganese ions and organic impurities. In the process, the cobalt and manganese ions are recovered by passing the extract obtained from the above-mentioned extraction through a column packed with a cation exchange resin to adsorb the cobalt and manganese ions on the cation exchange resin. The effluent containing bromine is then subjected to distillation to recover the bromine in the form of hydrobromic acid.

Further, Japanese Patent Application Publication No. 18577/1966 corresponding to British Pat. No. 899,288 discloses a process in which the mother liquor obtained from the reaction mixture of the liquid phase oxidation or the extract obtained by removing the solvent from the mother liquor by distillation and subjecting the distillation residue containing the oxidation catalyst to extraction with water or an aliphatic monocarboxylic acid is passed through a column packed with a cation exchange resin and through a column packed with an anion exchange resin, whereby the catalyst metal ions are adsorbed on the cation exchange resin to effect the recovery of them and bromine ions are adsorbed on the anion exchange resin to effect the recovery of them.

These conventional processes, however, have the following disadvantages.

(1) Since a cation exchange resin is used for the adsorption of heavy metal ions, an aqueous solution of a mineral acid such as hydrochloric acid, hydrobromic acid or sulfuric acid is usually used necessarily for the desorption and recovery of the adsorbed heavy metal ions, causing unnecessary components having adverse effects on the liquid phase oxidation to be incorporated into the recovered heavy metal compounds.

(2) Since the aqueous solution of the mineral acid is used for the desorption and recovery of the heavy metal ions, equipment therefor must be made of expensive corrosionresistant materials, leading to an increase in the construction cost of the equipment.

(3) Since the heavy metal ions and the halogen ions are independently recovered, the process is inevitably complicated.

(4) Although the halogen ions can be recovered, it is difficult to recover an organic halogen compound supplied as the reaction promotor and non-dissociative halogen compounds deemed to be produced during the oxidation reaction.

Accordingly, it has been anxiously desired to develop a process effective for recovering heavy metal ions or heavy metal ions and halogen values dissolved in solutions comprising a lower aliphatic monocarboxylic acid.

It is therefore a principal object of the present invention to provide an improved process for removing and/or recovering from a solution comprising a lower aliphatic monocarboxylic acid, heavy metal ions or heavy metal ions and halogen values dissolved therein.

Another object of the present invention is to provide a simplified process for removing heavy metal ion impurities simultaneously with the recovery of heavy metal ions as the liquid phase oxidation catalyst to enable the recovered catalyst heavy metal ions to be used repeatedly.

We conducted intensive research with a view to eliminating the foregoing defects of the conventional processes. As a result, we found that heavy metal ions or heavy metal ions and halogen ions are easily removed and/or recovered, from a lower aliphatic monocarboxylic acid solution containing various heavy metal ions, halogen ions and various organic compounds such as a reaction product and reaction intermediates, by contacting the lower aliphatic monocarboxylic acid solution with an anion exchange resin in the bromide or chloride state, while the water concentration in the lower aliphatic monocarboxylic acid solution has been adjusted to a level lower than 20% by weight, to adsorb on the anion exchange resin the heavy metal ions, together with halogen ions, which are anions. Also, we found that when an anion exchange resin mainly in the bromide or chloride state and partially in the lower aliphatic carboxylate state is used, even non-dissociative halogen compounds are adsorbed in the form of halogen ions on the anion exchange resin. We have now completed the present invention based on these findings. In this connection, it is noted that simultaneous recovery of heavy metal ions and halogen ions is also possible by the use of an anion exchange resin in the lower aliphatic carboxylate state, but the use of such an anion exchange resin is not practical because the amounts of heavy metal ions which can be adsorbed thereon are very small.

In accordance with the present invention, there is provided a process for recovering heavy metal ions or heavy metal ions and halogen values from a solution comprising a lower aliphatic monocarboxylic acid, which comprises the steps of:

(1) contacting a lower aliphatic carboxylic acid solution containing, dissolved therein, heavy metal ions of at least one member selected from the group consisting of vanadium, cobalt, chromium, manganese, nickel, copper, zinc, molybdenum and iron or containing, dissolved therein, said heavy metal ions and halogen values in the form of at least one member selected from the group consisting of bromine ions, chlorine ions, organic bromine compounds and organic chlorine compounds with an anion exchange resin, at least 60% of the ion-exchange groups of said anion exchange resin being in the bromide or chloride state, while the water concentration in the lower aliphatic monocarboxylic acid solution has been adjusted to a level lower than 20% by weight, thereby to adsorb the heavy metal ions or the heavy metal ions and the halogen values on the anion exchange resin; and (2) desorbing the adsorbed heavy metal ions or the adsorbed heavy metal ions and the adsorbed halogen values from the anion exchange resin by elution with an eluent. In the present invention, the halogen values remaining in the lower aliphatic monocarboxylic acid solution which has been contacted with the anion exchange resin can be further recovered by contacting the solution with another anion exchange resin or subjecting the solution to distillation.

According to the process of the present invention, heavy metal ions or heavy metal ions and bromine values and/or chlorine values can be easily recovered from solutions comprising a lower aliphatic monocarboxylic acid. Therefore, the process of the present invention is advantageously applicable to the recovery of catalyst heavy metal ions and promotor halogen values used for the liquid phase oxidation in a lower aliphatic monocarboxylic acid solvent and the simultaneous removal of impurities of heavy metal ions. In this connection, it is noted that the application of the process of this invention is not limited to that as described above. The process of this invention applies to any lower aliphatic monocarboxylic acid solution containing heavy metal ions or heavy metal ions and halogen values.

The foregoing and other objects, features and advantages of the present invention will be apparent to those skilled in the art from the following detailed description and appended claims taken in connection with the accompanying drawings in which:

Figure 4:
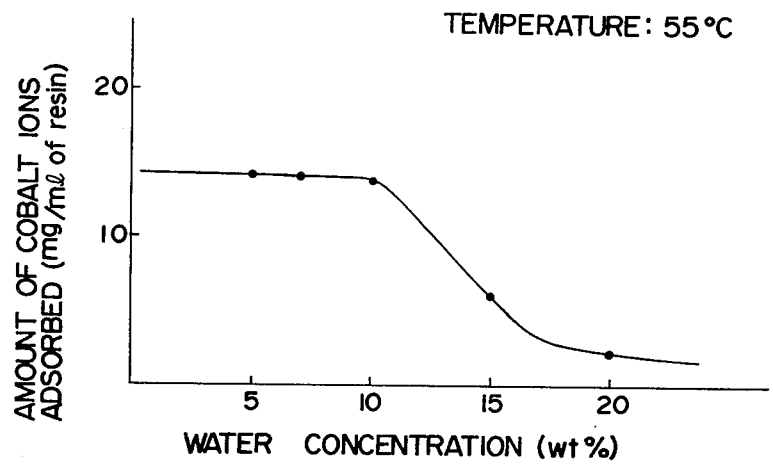
Figure 5:
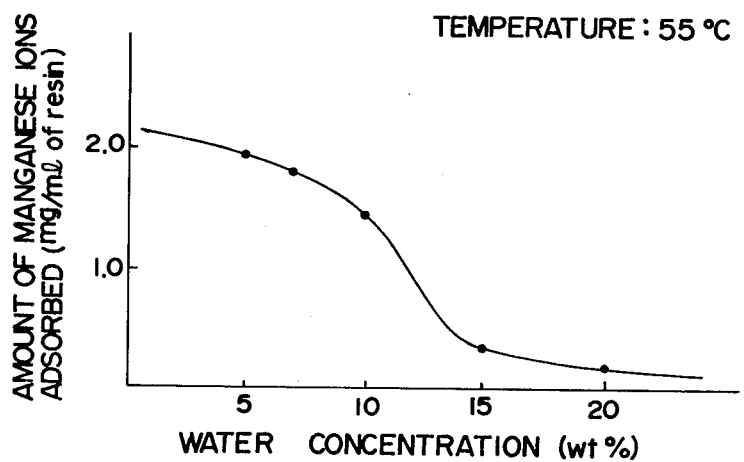

FIG. 4 is a graph illustrating the relationship between the water concentration in a lower aliphatic monocarboxylic acid solution and the amount of cobalt ions adsorbed on an anion exchange resin when the solution is contacted with the anion exchange resin at 55° C., which will be explained later with respect to Example 1; and FIG. 5 is a graph illustrating the relationship between the water concentration in a lower aliphatic monocarboxylic acid solution and the amount of manganese ions adsorbed on an anion exchange resin when the solution is contacted with the anion exchange resin at 55° C., which will be explained later with respect to Example 1.

Heavy metal ions that can be effectively removed and/or recovered from solutions comprising a lower aliphatic monocarboxylic acid according to the process of the present invention include ions of at least one member selected from vanadium, cobalt, chromium, manganese, nickel, copper, zinc, molybdenum and iron.

As described hereinbefore, by the term "halogen values" are meant those halogens in the form of inorganic bromine or chlorine ions or organic non-dissociative bromine or chlorine compounds. These halogen values can also be effectively removed and/or recovered from solutions comprising a lower aliphatic monocarboxylic acid according to the process of the present invention.

All kinds of mother liquors obtained by separating undissolved products, intermediates and other solids from the reaction mixtures formed by liquid phase oxidation of substituted benzenes in a lower aliphatic monocarboxylic acid solvent in the presence of a heavy metal catalyst system and a halogen compound as the reaction promotor (these mother liquors will often be referred to as "mother liquor of reaction mixture" hereinafter) may be lower aliphatic monocarboxylic acid solutions to be treated according to the process of the present invention. For example, there can be mentioned mother liquors of reaction mixtures derived from the liquid phase oxidation of substituted benzenes having 1 to 4 substituents which benzenes are those substituted with at least one member selected from the group consisting of $C_1$–$C_3$ alkyl, aldehyde and carboxyl on condition that a benzene substituted with carboxyl is further substituted with at least one substituent other than carboxyl. Specific examples of mother liquors of reaction mixtures include those derived from the process for preparing terephthalic acid from p-xylene, those derived from the process for preparing terephthalic acid from p-tolualdehyde, toluic acid or p-diisopropylbenzene and those derived from the process for preparing an aromatic carboxylic acid, such as benzoic acid, isophthalic acid, phthalic acid or trimellitic acid, from the corresponding starting material such as toluene, m-xylene, o-xylene or pseudocumene. In addition, extracts containing heavy metal ions or heavy metal ions and halogen values, which have been obtained by distilling off the solvent from the above-mentioned mother liquors and extracting the residues with a mixture of water and a lower aliphatic monocarboxylic acid, may also be lower aliphatic monocarboxylic acid solutions to be treated according to the process of the present invention.

The above-mentioned lower aliphatic monocarboxylic acid solutions are usually composed of a mixture comprising a lower aliphatic monocarboxylic acid used as the solvent, a heavy metal catalyst, halogen values, various organic compounds such as a desired reaction product, unreacted starting material, intermediates and by-products, small amounts of impurity metal ions formed by corrosion of a reaction apparatus and the like and a considerable amount of water formed by the reaction.

Figure 1:
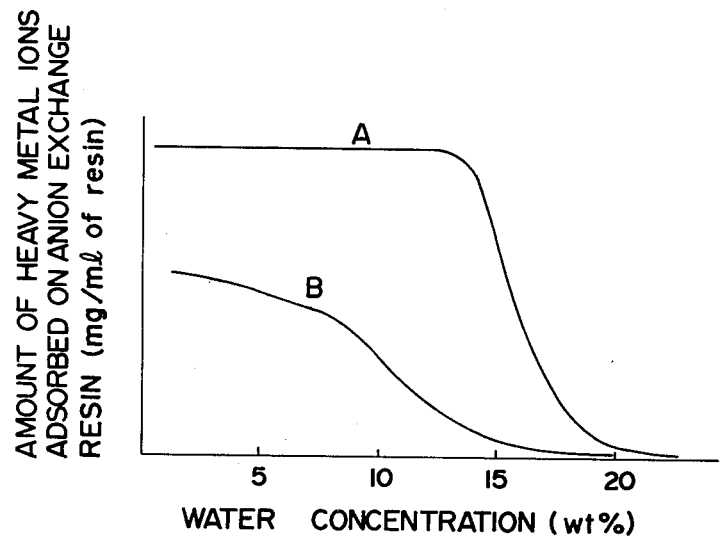
FIG. 1 is a graph illustrating the typical relationship between the water concentration in a lower aliphatic monocarboxylic acid solution and the amount of heavy metal ions adsorbed on an anion exchange resin when the solution is contacted with the anion exchange resin.

In practicing the process of the present invention, the water concentration in the lower aliphatic monocarboxylic acid solution has a significant influence on adsorption efficiency. Usually when the water concentration is 20% by weight or more, the amount of heavy metal ions adsorbed on an anion exchange resin per unit volume thereof is drastically reduced, although the critical water concentration differs to some extent depending on such factors as the halogen ion concentration, the adsorption temperature and the kind of anion exchange resin. A typical instance of the relationship between the water concentration in the lower aliphatic monocarboxylic acid solution and the amount of heavy metal ions adsorbed on the anion exchange resin per unit volume thereof is illustrated in FIG. 1, from which it will readily be understood that at a water concentration of 20% by weight or more, the adsorption efficiency is drastically reduced. In the process of the present invention, therefore, in order to recover heavy metal ions at a high efficiency, it is indispensable that the water concentration in the lower aliphatic monocarboxylic acid solution to be contacted with an anion exchange resin should be less than 20% by weight. The preferred water concentration is less than 15% by weight. The lower limit of the water concentration is not particularly critical, and therefore, the water concentration may be substantially 0% by weight.

In the liquid phase oxidation in which a lower aliphatic monocarboxylic acid is used as the solvent, a halogen, especially bromine, is usually used as an oxidation promotor. As the source of bromine, there may be used inorganic bromine compounds such as cobalt bromide, manganese bromide molecular bromine and hydrobromic acid, and organic bromine compounds such as 1,1,2,2-tetrabromoethane, $\alpha,\beta,\alpha',\alpha'$,-tetrabromo-p-xylene, bromoform and bromoacetic acid. Also, chlorine may be used as the oxidation promotor. As the source of chlorine, there may be used hydrogen chloride, cobalt chloride, manganese chloride, molecular chlorine and chloroacetic acid. According to the process of the present invention, halogen values derived from these promotors can be effectively recovered.

As the lower aliphatic monocarboxylic acid having 2 to 4 carbon atoms, that is used as the solvent in the liquid phase oxidation, there can be mentioned, for example, acetic acid, propionic acid and butyric acid. Acetic acid and propionic acid are frequently used, and acetic acid is most popularly used as the solvent.

Any of weakly basic anion exchange resins of the primary amine, secondary amine or tertiary amine type and strongly basic anion exchange resins of the quaternary ammonium type may be used in the present invention. Anion exchange resins are usually prepared by chloromethylation of a styrene-divinylbenzene copolymer and subsequent amination of the chloromethylated styrene-divinylbenzene copolymer with a primary, secondary, or tertiary alkylamine. Pyridine type anion exchange resins are prepared by copolymerizing vinylpyridine and divinylbenzene as disclosed in Japanese Patent Application Laid-Open Specification No. 71790/1973. The pyridine type anion exchange resins are often further subjected to alkylation to provide a quaternary ammonium type anion exchange resin. Primary amine type anion exchange resins are prepared, for example, by nitration of a styrenedivinylbenzene copolymer and subsequent reduction of the nitrated copolymer. In practicing the process of the present invention, strongly basic anion exchange resins of the quaternary ammonium type are preferred. Also, anion exchange resins having pyridine rings are preferred.

As commercially available products composed of these anion exchange resins, there can be mentioned Amberlite (trade mark) IRA-938, IRA-910, IRA-904, IRA-900, IRA-400, IRA-401, IRA-402, IRA-410, IRA-411, A-26 and A-27 (manufactured by Rohm & Haas Company, U.S.A.), Dowex (trade mark) 1, 2, 21K, 11, MSA-1, I×4 and II×8 (manufactured by the Dow Chemical Company, U.S.A.), Amberlite (trade mark) IR-45 and IRA-68 (manufactured by Rohm & Haas Company, U.S.A.), Ionac (trade mark) A-580 and A-590 (manufactured by American Cyanamid Company, U.S.A.), and Dia Ion (trade mark) 306, 316, 318, 406, 412 and 418 (manufactured by Mitsubishi Chemical Industries Limited, Japan).

In these anion exchange resins, the degree of cross-linking as defined in terms of the amount (% by weight based on the monomer mixture) of a crosslinking agent such as divinylbenzene incorporated at the start of the copolymerization reaction may may be 2 to 30, preferably 4 to 20. From the viewpoint of the ion-adsorption speed, the particle size of the anion exchange resin may be 15 to 400 mesh, preferably 20 to 200 mesh. Either gel-type anion exchange resins such as Dowex 1 and 2 and Amberlite IRA-410 and IRA-400 or porous anion exchange resins such as Dia Ion 306, 316 and 318, Dowex MSA-1 and Amberlite IRA-910, IRA-411 and IRA-938 may be used in the present invention. These anion exchange resins are usually in the chloride state and can be easily converted into those in the bromide state as will be described hereinafter.

Contact of the lower aliphatic monocarboxylic acid solution with the anion exchange resin may be effected either batchwise or chromatographically. From the industrial viewpoint, it is preferred to effect the contact chromatographically by passing the solution through a column packed with the anion exchange resin, because of its high adsorption efficiency.

Heavy metal ions or heavy metal ions and halogen ions, which have been adsorbed on the anion exchange resin, can be desorbed and recovered according to a customary elution method in which there is used an aqueous solution containing a mineral acid such as sulfuric acid, nitric acid or hydrochloric acid or an aqueous solution containing an alkali such as sodium hydroxide or potassium hydroxide. However, in case the recovered heavy metal ions or the recovered heavy metal ions and halogen ions are recycled and reused as the catalyst or as the catalyst and promotor, in order to avoid incorporation of sulfate ions, nitrate ions or sodium ions into the eluate and enable the recovered catalyst or the recovered catalyst and promotor to be easily recycled and reused, it is preferred to effect elution by using as an eluent water or a mixture of a lower aliphatic monocarboxylic acid and at least 15% by weight of water. Of course, elution can be effected by using as an eluent a mixture of a lower aliphatic monocarboxylic acid and water in an amount of less than 15% by weight. However, in this case, a very large amount of the eluent is necessary, and hence, the use of such an eluent is not preferred from the industrial viewpoint. In general, a condenser is often disposed at the top of a reaction vessel for liquid phase oxidation to remove the reaction heat. A mixture of water and a lower aliphatic monocarboxylic acid, condensed and obtained in this condenser, can be used as the eluent as it is or after it is diluted with an appropriate amount of water.

The elution temperature is, of course, restricted by the thermal stability of the anion exchange resin. However, even anion exchange resins which are ordinarily regarded as having poor thermal stability are relatively stable in aliphatic monocarboxylic acids, and hence, the elution temperature may be chosen within a relatively broad range of from room temperature to about 120° C.

In the present invention, organic halogen compounds contained as the source of a halogen in the lower aliphatic monocarboxylic acid solution, such as benzyl bromide, bromoacetic acid, chloroacetic acid and $\alpha,\alpha,\alpha',\alpha'$-tetrabromo-pxylene, and non-dissociative halogen compounds of an unknown structure formed by the oxidation reaction, can also be adsorbed on anion exchange resins. It is believed that the adsorption is probably due to the ion exchange accompanied by the hydrolysis of the halogen compound. From the viewpoints of the durability, in relation with heat resistance, of the anion exchange resin and the ion exchange speed, it is preferred that the adsorption of these halogen compounds be carried out at a temperature of 30° to 120° C., especially 50° to 100° C.

It is conceivable to use an anion exchange resin in the halide state, in the hydroxide state, in the lower aliphatic monocarboxylate state such as in the acetate state or in the combined state thereof before the resin is contacted with a lower aliphatic monocarboxylic acid solution to be treated. In general, however, the use of an anion exchange resin in the bromide or chloride state is advantageous because the amount of heavy metal ions adsorbed on the anion exchange resin per unit volume thereof is large. Particularly when the heavy metal ions to be adsorbed on an anion exchange resin are cobalt and/or manganese ions, the amount of those ions adsorbed on an anion exchange resin in the bromide or chloride state is very large, while the amount of those ions adsorbed on an anion exchange resin in the hydroxide or lower aliphatic monocarboxylate state is extremely small. Accordingly, from the viewpoint of adsorbability of cobalt and/or manganese ions, it is indispensable in this invention that at least 60% of the ion-exchange groups of an anion exchange resin should be in the bromide or chloride state. Such an anion exchange resin is especially suitable for mother liquors of reaction mixtures derived from the liquid phase oxidation of p-xylene by means of air in the presence of a cobalt and/or manganese catalyst together with a bromine promotor, because cobalt and/or manganese ions are selectively adsorbed on the anion exchange resin at a high efficiency to separate cobalt and/or manganese ions from other impurity heavy metal ions formed by corrosion of the reaction apparatus or the like, such as iron, chromium and/or nickel ions. It is preferred that 85% or more of the ion-exchange groups of the anion exchange resin be in the bromide or chloride state. Also, it is to be noted that the use of an anion exchange resin in the bromide state is especially preferred.

By way of example, methods of converting an ordinary anion exchange resin into an anion exchange resin in the bromide state will now be explained. A commercially available anion exchange resin is packed in a column, and an aqueous solution containing 1 to 10% by weight of an alkali such as sodium hydroxide is passed, in an amount at least 50 times by volume as large as that of the packed resin, through the column over a period of at least 30 minutes. Then, the resin is washed with deionized water in an amount about 10 times by volume as large as that of the packed resin over a period of at least 10 minutes. An acetic acid solution containing hydrobromic acid in such an amount as will provide the bromide ion concentration of about 2% by weight is passed, in an amount at least 10 times by volume as large as that of the packed resin, through the column over a period of at least 30 minutes. Thus, substantially all of the ion-exchange groups of the anion exchange resin are converted into those in the bromide state. If deionized water is then passed through the column at a space velocity of 1 to 20 hr$^{-1}$, the ion-exchange groups in the bromide state are gradually converted into those in the hydroxide state to provide an anion exchange resin partially in the hydroxide state. In the case of an ordinary strong base anion exchange resin, the proportion of the ion-exchange groups in the bromide state relative to the total ion-exchange groups can be reduced to about 75 to about 80% by the above-mentioned washing treatment with deionized water. If it is desired to further reduce the proportion of the ion-exchange groups in the bromide state relative to the total exchange groups, the anion exchange resin is washed with an aqueous solution containing about 1% by weight of sodium hydroxide. Thus, the proportion of the ion-exchange groups in the bromide state relative to the total ion-exchange groups can be optionally controlled depending upon the amount of the aqueous sodium hydroxide solution. It is also possible to provide an anion exchange resin substantially completely in the hydroxide state.

In the case of a vinylpyridine type anion exchange resin as disclosed in Japanese Patent Application Laid-Open Specification No. 71790/1973, the proportion of the ion-exchange groups in the bromide state relative to the total ion-exchange groups can be optionally controlled by contacting the resin with an adequate aqueous solution having a bromine concentration adjusted within the range of from 1,000 ppm to 5% by weight instead of the above-mentioned acetic acid solution containing hydrobromic acid. The above-mentioned methods are chromatographical ones, but batch-wise methods may alternatively be adopted.

An anion exchange resin in the lower aliphatic carboxylate state is easily obtained by contacting an anion exchange resin in the hydroxide state with the corresponding lower aliphatic carboxylic acid.

In case the lower aliphatic monocarboxylic acid solution contains not only cobalt and/or manganese ions but also other heavy metal ions, if an anion exchange resin in the bromide or chloride state is employed, cobalt and/or manganese ions are selectively absorbed on the resin but other heavy metal ions are hardly absorbed on the resin. Accordingly, cobalt and/or manganese ions can be separated from other heavy metal ions at a high efficiency. These heavy metal ions are left as the distillation residue even after the subsequent distillation as described hereinafter. If the recovery of these heavy metal ions is desired, the lower aliphatic monocarboxylic acid solution after contacted with the anion exchange resin, which is substantially free of cobalt and/or manganese ions, may be treated again with an anion exchange resin in the bromide or chloride state, whereby heavy metal ions can be adsorbed on the resin and recovered at a high efficiency.

Since an anion exchange resin in the bromine state has an especially high ability to adsorb thereon cobalt and/or manganese ions selectively in large amounts per unit volume of the resin and hence the utilization efficiency of the resin is very high, the use of such an anion exchange resin is preferred, from the economical viewpoint, especially for mother liquors of reaction mixtures derived from the ordinary liquid phase oxidation of p-xylene in the conjoint presence of a cobalt-manganese catalyst and a bromine promotor. Therefore, according to one preferred embodiment of this invention for the recovery of the catalyst and the promotor from the mother liquors of the reaction mixtures derived from the ordinary liquid phase oxidation of p-xylene, cobalt, manganese and bromine ions and parts of non-dissociative bromine compounds are recovered from the mother liquor by using an anion exchange resin in which at least 60%, preferably at least 85%, of the total ion-exchange groups is in the bromide state (step 1), and the resulting mother liquor is further contacted with another anion exchange resin in the lower aliphatic monocarboxylate state such as in the acetate state or in the hydroxide state whereby the remaining non-dissociative bromine compounds are adsorbed in the form of bromine ions on the resin to effect the recovery of bromine (step 2). When the amounts of the remaining non-dissociative bromine compounds in the mother liquor after the step 1 are small, the further contact of the mother liquor with the anion exchange resin in the lower aliphatic monocarboxylate state or in the hydroxide state may be omitted or only part of the mother liquor may be contacted with the anion exchange resin as used in the step 2, with overall economical factors being taken into consideration.

According to another preferred embodiment of the present invention, the mother liquor of the reaction mixture is contacted with an anion exchange resin in the bromide state and the resulting mother liquor is subjected to distillation to effect the recovery of the remaining non-dissociative bromine compounds. The lower aliphatic monocarboxylic acid and the non-dissociative bromine compounds may be simultaneously recovered by distillation. But usually, this recovery is accomplished by two-step distillation. In the first step distillation, the majority of the lower aliphatic monocarboxylic acid is distilled off, and in the second step distillation, the non-dissociative bromine compounds are distilled while the reaction product, intermediates, non-volatile materials and heavy metal impurities are removed as the distillation residue. As a result of our investigations on conditions of such distillation, it was found that the recovery rate of the non-dissociative bromine compounds is greatly influenced by the distillation conditions in the second step distillation and that a high recovery is attained when the relationship between the vapor temperature t and the pressure p at the second step distillation satisfies the requirement represented by the following equation (1):

$$\log p \leq 9.57 - \frac{3330}{t + 348} \quad (1)$$

wherein p stands for pressure (mmHg absolute) and t stands for the vapor temperature (°C.).

The second step distillation is accomplished by using known distillation apparatus such as a batch type distillation column, a rotary type distillation column, a forced circulation evaporator, a kettle distillation column, a packed fractionating column, a pot still, a multi-tray type distillation column, a bubble cap column, a thin film distillation column, a centrifugal evaporator, a rotary thin layer evaporator, a molecular still and a flash evaporator. In general, the concentrate of the mother liquor of the reaction mixture to be fed to the distillation apparatus as used in the second step distillation is highly viscous because it contains non-volatile organic materials and heavy metal impurities at high concentrations. Accordingly, it is preferred that the distillation be carried out by using a rotary thin layer evaporator. When a rotary thin layer evaporator is employed, if the distillation is conducted under such conditions that the relationship between the pressure in the column and the vapor temperature satisfies the requirement of the above equation (1) on the assumption that the temperature of the cylinder of the distillation column is the vapor temperature, the non-dissociative bromine compounds are, of course, recovered in high yield.

Two kinds of distillation apparatuses may be employed for practicing the above-mentioned two-step distillation. However, it is also possible to use only one distillation apparatus. In this case, the lower aliphatic monocarboxylic acid is mainly distilled and recovered first, and the remaining lower aliphatic monocarboxylic acid and non-dissociative bromine compounds are then distilled and recovered to separate them from the distillation residue composed of non-volatile by-products formed by the oxidation, heavy metal impurities and the like. The distillation may be conducted under elevated pressure, atmospheric pressure or reduced pressure. From the economic viewpoint, it is preferred that the distillation for the recovery of the lower aliphatic monocarboxylic acid be carried out under atmospheric pressure and the distillation for the recovery of non-dissociative bromine compounds be carried out under a pressure of 0.1 to 800 mmHg. Distillation under a pressure higher than 800 mmHg is not preferred because the cost of the distillation apparatus becomes inevitably high. During the distillation for the recovery of the non-dissociative bromine compounds, in general, the mother liquor of the reaction mixture is gradually concentrated to increase the viscosity and cause precipitation of solids, resulting in poor operability. Accordingly, it is preferred that the distillation be carried out after or while incorporating a high boiling point solvent into the concentrated mother liquor as is well known in the art.

As will be apparent from the foregoing illustration, according to the process of the present invention, heavy metal ions or heavy metal ions and halogen values in a lower aliphatic monocarboxylic acid solution can be adsorbed on an anion exchange resin in the bromide or chloride state and recovered with ease by elution. Even non-dissociative halogen compounds can be adsorbed, in the form of bromine ions, on the anion exchange resin, and the non-dissociative halogen compounds remaining in the resulting solution can be recovered at a high recovery by contacting the solution with another anion exchange resin to adsorb them thereon or by subjecting the solution to distillation. Further, in case the separation and recovery of only cobalt and/or manganese ions among heavy metal ions is intended, cobalt and/or manganese ions can be simply separated from other heavy metal ions by the use of an anion exchange resin in the bromide or chloride state. Accordingly, the process of the present invention for the recovery of heavy metal ions or heavy metal ions and halogen values in lower aliphatic monocarboxylic acid solutions is very advantageous from the economic viewpoint and will make a great contribution to the art.

The present invention will now be described in detail by reference to the following Examples that by no means limit the scope of the invention. In Examples, all of "%" are by weight unless otherwise indicated.

In Examples, quantitative analyses were conducted as follows.

(1) The concentrations of metal ions were determined using an Atomic-Absorption/Spectrophotometer Model 170-10 (trade mark of a product manufactured by Hitachi Ltd., Japan)

(2) The total bromine concentrations were determined using an X-Ray Spectrometer KG-3 (trade mark of an X-ray fluorescence analyzer manufactured and sold by Rigaku Corp., Japan).

(3) The concentrations of halogen ions such as bromine ions or chlorine ions were determined by colorimetric method of Utsumi [Journal of the Chemical Society of Japan, Chemistry and Industrial Chemistry, 73, 838-841 (1952)]. The method is as follows:

1 ml of a sample, 1 ml of a 0.3% ethanol solution of mercury thiocyanate and 2 ml of a 6% solution of iron alum dissolved in a 6 N aqueous acid solution were charged into a 100 ml graduated flask, and pure water was added thereto so that the total volume of the resulting solution was 100 ml. The absorbance of the resulting solution was measured at 460 m$\mu$ and the concentration of halogen ions was determined using the calibration curve which had been previously prepared.

In the following Examples, the term "starting solution" is intended to mean a lower aliphatic monocarboxylic acid solution containing heavy metal ions or heavy metal ions and halogen values to be adsorbed on an anion exchange resin according to the process of this invention.

EXAMPLE 1

Figure 2:
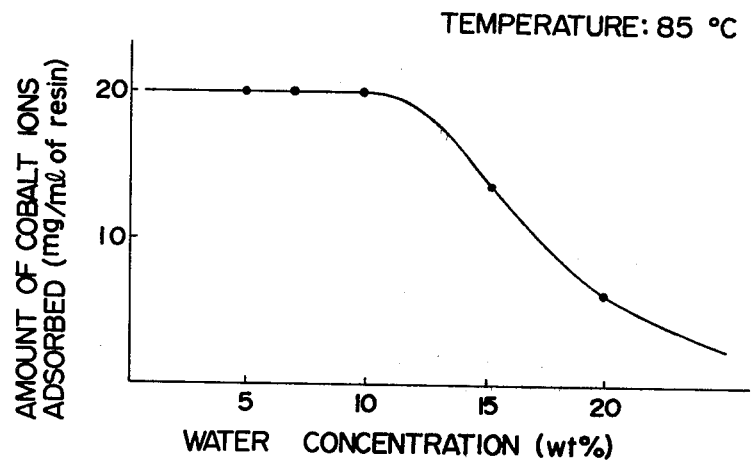
FIG. 2 is a graph illustrating the relationship between the water concentration in a lower aliphatic monocarboxylic acid solution and the amount of cobalt ions adsorbed on an anion exchange resin when the solution is contacted with the anion exchange resin at 85° C., which will be explained later with respect to Example 1.
Figure 3:
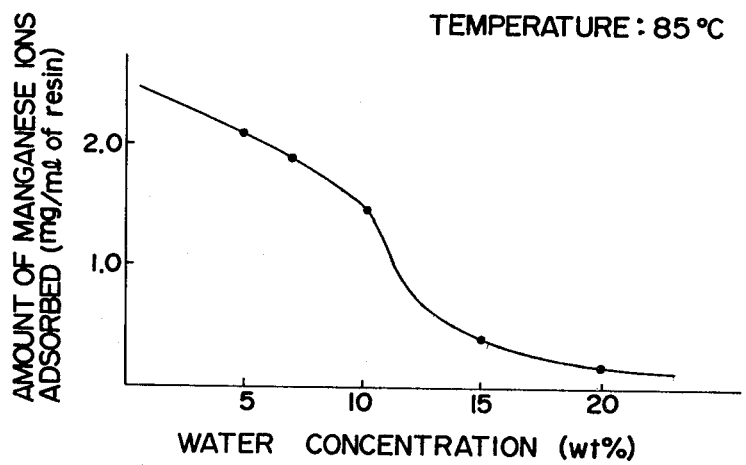
FIG. 3 is a graph illustrating the relationship between the water concentration in a lower aliphatic monocarboxylic acid solution and the amount of manganese ions adsorbed on an anion exchange resin when the solution is contacted with the anion exchange resin at 85° C., which will be explained later with respect to Example 1.

An anion exchange resin Dowex II×8 was sufficiently washed with a 10% aqueous solution of sodium hydroxide in an amount 50 times by volume as large as that of the resin and then washed with water. The anion exchange resin in a wet state was divided into five portions each having a weight of about 15 g, and the five divided portions of the resin were respectively charged into five columns equipped with a glass jacket and maintained at 55° C. Then, 500 ml of an acetic acid solution containing 4% of 47% hydrobromic acid were passed through each column to convert the anion exchange resin into an anion exchange resin in the bromide state. Five kinds of acetic acid solutions each containing 500 ppm of cobalt ions, 150 ppm of manganese ions and 1,200 ppm of bromine ions, but having varied water concentration of 5, 7, 10, 15 and 20%, respectively, were prepared by using cobalt (II) acetate, manganese (II) acetate, 47% hydrobromic acid, deionized water and acetic acid. Then, 3 liters each of these five solutions were passed at a rate of 1 liter/hr through the column, while maintaining the column temperature at 85° C. After completion of passage of the solution, compressed air was fed for about 30 seconds to the column at the top thereof to remove the solution left in the column in spaces between the resin particles. Then 500 ml of distilled water were fed at a rate of 1 liter/hr to the column to recover the adsorbed cobalt and manganese ions. The cobalt and manganese ion concentrations in the eluate from the column were determined. The influence of the water concentration in the abovementioned acetic acid solution on the amounts of cobalt and manganese ions adsorbed on the anion exchange resin per unit volume thereof were examined to obtain the results as shown in FIGS. 2 and 3.

The foregoing procedures were repeated except that the adsorption temperature was 55° C. The influence of the water concentration in the acetic acid solution on the amounts of cobalt and manganese ions adsorbed on the anion exchange resin per unit volume thereof were similarly examined to obtain the results as shown in FIGS. 4 and 5.

As will be apparent from the results as shown in FIGS. 2 to 5, if the water concentration in the acetic acid solution is 20% or more, both the cobalt ions and the manganese ions are hardly adsorbed on the anion exchange resin in the bromide state.

On the other hand, the bromine ion concentration in each of the first eluates as obtained above was determined. 200 ml of a 2% aqueous solution of sodium hydroxide were passed through each of the columns packed with the resin as used in the preceding procedures to obtain a second eluate. The bromine ion concentration in each of the second eluates from the columns was determined. The total amount of bromine ions was obtained, with respect to each of the five solutions, by calculation from the bromine ion concentrations in the first and second eluates. The amount of bromine ions adsorbed on the resin simultaneously with the adsorption of cobalt and manganese ions was determined by subtracting from the total amount of bromine ions the amount of bromine ions which the anion exchange resin in the bromide state had in itself. The obtained results are shown in Table 1 in which "Temperature" is an adsorption temperature (column temperature) and "Water Concentration" is that in an acetic acid solution before adsorption treatment.

TABLE 1

| Temperature (°C.) | Amount (mg/ml of resin) of Bromine Ions adsorbed | | | | |
|---|---|---|---|---|---|
| | Water Concentration (wt %) | | | | |
| | 5% | 7% | 10% | 15% | 20% |
| 55 | 45 | 43 | 42 | 14 | 6 |
| 85 | 58 | 56 | 53 | 34 | 17 |

EXAMPLE 2

Four kinds of anion exchange resins Dowex I×4, Dia Ion 318, Dowex 21K and Ionac A-580 were converted to those in the bromide state in the same manner as described in Example 1, and packed respectively in glass columns each having a height of 50 cm and equipped with a jacket. The amount of resin packed in each of columns was 130 ml. 2.6 liters of an acetic acid solution prepared by using cobalt (II) acetate, hydrobromic acid, bromoacetic acid, acetic acid and deionized water [cobalt ion concentration: 500 ppm, bromine ion concentration: 430 ppm, total bromine concentration (the sum of the bromine ion concentration and the non-dissociative bromine concentration): 1150 ppm, water concentration: 7%] were passed at a space velocity of 2 hr$^{-1}$ through each column and 500 ml of water were passed at the same velocity through the column. The acetic acid solution and water were alternately passed in succession through the column by repeating the above procedures, and the bromine ion, total bromine and cobalt ion concentrations in the respective effluents were analyzed in detail to determine the relationship between the proportion of the ion-exchange groups in the bromide state of the anion exchange resin and the breakthrough adsorbing capacity of the anion exchange resin to cobalt ions.

In order to reduce the proportion of the ion-exchange groups in the bromide state of each of the above-mentioned anion exchange resins in the bromide state, an aqueous solution containing 2% of sodium hydroxide was passed through a column packed with the resin which column was of the same type as described above, to effect partial elution of bromine ions, and in the same manner as described above, the relationship between the proportion of the ion-exchange groups in the bromide state and the breakthrough adsorbing capacity to cobalt ions was determined. The obtained results are shown in Table 2.

TABLE 2

| Proportion (%) of Ion-Exchange Groups in the Bromide State* | Breakthrough Adsorbing Capacity (mg/ml of resin) to Cobalt Ions | | | |
|---|---|---|---|---|
| | Dowex I × 4 | Dia Ion 318 | Dowex 21K | Ionac A-580 |
| 100 | 4.1 | 5.4 | 6.5 | 5.5 |
| 85 | 3.5 | 4.6 | 5.5 | 4.8 |
| 60 | 2.5 | 3.1 | 2.8 | 1.8 |
| 40 | 0.9 | 1.5 | 1.9 | 0.7 |

Note
*The proportion of the ion-exchange groups in the bromide state to the total exchange groups before passage of the acetic acid solution (the average value of the total resin in the column)

From the results as shown in Table 2, it will readily be understood that the breakthrough adsorbing capacity to cobalt ions increases as the proportion of the ion-exchange groups in the bromide state to the total ion-exchange groups of a anion exchange resin becomes high.

On the other hand, the amounts of bromine ions adsorbed on the anion exchange resins by the first passage of 2.6 liters of the above-mentioned acetic acid solution were as shown in Table 3.

TABLE 3

| Proportion (%) of Ion-Exchange Groups in the Bromide State | Amount (mg/ml of resin) of Bromine Ions Adsorbed | | | |
|---|---|---|---|---|
| | Dowex I × 4 | Dia Ion 318 | Dowex 21 K | Ionac A-580 |
| 100 | 7.6 | 7.9 | 8.3 | 8.1 |
| 85 | 12 | 11 | 13 | 12 |
| 60 | 14 | 15 | 17 | 13 |
| 40 | 17 | 18 | 20 | 16 |

EXAMPLE 3

A vinylpyridine type anion exchange resin (crosslinking degree=20, particle size=100—200 mesh) was prepared according to the method as disclosed in Japanese Patent Application Laid-Open Specification No. 71790/1973. Then, 2 liters of the resin were washed with 100 liters of a 10% aqueous solution of sodium hydroxide to convert the resin into an anion exchange resin in the hydroxide state, and 50 ml of the anion exchange resin were charged into each of five glass columns having an internal diameter of 3 cm and equipped with a jacket. Four kinds of aqueous solutions having bromine ion concentrations of 5%, 4,000 ppm, 1,500 ppm and 1,300 ppm, respectively, were prepared by using 47% hydrobromic acid and deionized water. Then, 5 liters each of these solutions were passed through each of four of the resin-packed column. Thus, there were prepared four columns respectively packed with anion exchange resins having varied proportions of the ion-exchange groups in the bromide state to the total ion-exchange groups, namely, 100%, 90%, 50% and 40%. 25 liters of an acetic acid solution having a water concentration of 8.1% and a manganese concentration of 152 ppm were prepared by using manganese (II) acetate, deionized water and acetic acid, and 5 liters of the solution were passed through each of the four columns as well as the column packed with the resin in the hydroxide state. The amount of manganese ions adsorbed on each anion exchange resin per unit volume thereof was determined to obtain the results as shown in Table 4.

TABLE 4

| | Ionic State of Anion Exchange Resin | | |
|---|---|---|---|
| Run No. | Amount (meq/ml) Bromine Ions Adsorbed | Proportion (%) of Ion-Exchange Groups in the Bromide State | Amount (mg/ml of resin) of Manganese Ions Adsorbed |
| 1 | 2.5 | 100 | 5.4 |
| 2 | 2.25 | 90 | 3.2 |
| 3 | 1.25 | 50 | 0.70 |
| 4 | 0.50 | 35 | 0.18 |
| 5 | 0 | 0 | 0.10 |

From the results as shown in Table 4, it will readily be understood that the amount of manganese ions adsorbed is decreased as the proportion of the ion-exchange groups in the bromide state relative to the total ion-exchange groups of the anion exchange resin is reduced and the proportion of the ion-exchange groups in the hydroxide state is increased instead, and that when the proportion of the ion-exchange groups in the bromide state is lower than 50%, the anion exchange resin cannot be practically used for the adsorption of manganese ions.

EXAMPLE 4

By using 150 ml each of three commercially available anion exchange resins as indicated in Table 5 and two vinylpyridine type anion exchange resins prepared according to the method as disclosed in Japanese Patent Application Laid-Open Specification No. 71790/1973, anion exchange resins in the bromide state and in the acetate state with respect to each starting anion exchange resin were prepared. The anion exchange resins in the bromide state were prepared by using an 10% aqueous solution of sodium hydroxide and an aqueous solution having a bromine ion concentration of 5% in substantially the same manner as described in Example 3. The anion exchange resins in the acetate state were prepared by washing the anion exchange resins in the hydroxide state as prepared in substantially the same manner as described in Example 3, with acetic acid in an amount 20 times or more by volume as large as that of the resin. Then, with respect to each resin, the amount of cobalt ions adsorbed at a temperature of 85° C. was determined in the same manner as described in Example 1 by using an acetic acid solution having a cobalt ion concentration of 510 ppm and a water concentration of 7.5%, which had been prepared by using cobalt (II) acetate, deionized water and acetic acid. The obtained results are shown in Table 5.

TABLE 5

| Run No. | Anion Exchange Resin Kind | Particle Size (mesh) | Amount (mg/ml of resin) of Cobalt Ions Adsorbed Bromide State | Acetate State |
|---|---|---|---|---|
| 1 | Amberlite IRA-411 | 20–50 | 6.3 | 1.1 |
| 2 | Dowex 1 × 4 | 20–50 | 7.2 | 1.9 |
| 3 | Amberlite IRA-68 | 20–50 | 4.3 | 0.7 |
| 4 | Vinylpyridine type (crosslinking degree = 20) | 100–200 | 13.7 | 4.1 |
| 5 | Vinylpyridine type (crosslinking degree = 10) | 100–200 | 11.3 | 3.8 |

As will be apparent from the results as shown in Table 5, anion exchange resins in the acetate state have a much lower adsorbing capacity than those in the bromide state and they cannot be practically used. It will also be apparent that a weakly basic resin, IRA-68, is relatively poor in the adsorbing capacity.

EXAMPLE 5

An anion exchange resin Dowex II×8 (particle size = 50–100 mesh) was contacted batchwise with a 0.5% aqueous solution of sodium hydroxide in an amount 10 times by volume as large as that of the resin and was then washed with acetic acid to obtain an anion exchange resin in which 70% of the ion-exchange groups was in the chloride state. Then, a glass column having an internal diameter of 40 mm and a height of 2,000 mm and equipped with a jacket was packed with the so obtained anion exchange resin to a height of 1,600 mm and the column temperature was maintained at 85° C. Water, potassium molybdate, vanadium pentoxide, ferric chloride, chromium (II) acetate, nickel (II) acetate and 36% hydrochloric acid were added to acetic acid to prepare as a starting solution an acetic acid solution having a water concentration of 3.5% and concentrations of metal ions and chlorine ions as indicated in Table 4. Then, 40 liters of the so prepared acetic acid solution were passed through the above glass column at a rate of 2 liters/hour. The concentrations of metal ions and chlorine ions in the effluent were determined to obtain the results as shown in Table 6. Then, 10 liters of water were passed through the column at a rate of 2 liters/hour to obtain an eluate having concentrations of metal ions and chlorine ions as shown in Table 6.

TABLE 6

| | Ion Concentrations (ppm) | | | | | |
|---|---|---|---|---|---|---|
| | Mo | V | Fe | Cr | Ni | Cl⁻ |
| Starting Solution | 255 | 180 | 233 | 226 | 221 | 2000 |
| Effluent | <1 | <1 | 3 | 5 | 22 | 1350 |
| Eluate | 15 | 32 | 555 | 890 | 801 | 2100 |

EXAMPLE 6

The experiments were conducted in the same manner as described in Example 5 except that propionic acid was used instead of acetic acid for the washing of the anion exchange resin and the preparation of a starting solution and the concentrations of metal ions and chlorine ions in the starting solution were as indicated in Table 7. The water concentration in the starting solution was 3%. The concentrations of metal ions and chlorine ions in the starting solution, the effluent and the eluate are shown in Table 7.

TABLE 7

| | Ion Concentration (ppm) | | | | | |
|---|---|---|---|---|---|---|
| | Mo | V | Fe | Cr | Ni | Cl⁻ |
| Starting Solution | 240 | 185 | 217 | 36 | 42 | 800 |
| Effluent | <1 | <1 | 1.5 | <1 | <1 | <1 |
| Eluate | 11 | 45 | 860 | 111 | 165 | 1610 |

From the results as shown in Table 6 and 7, it will readily be understood that both the heavy metal ions and the chlorine ions contained in a lower aliphatic monocarboxylic acid solution are simultaneously adsorbed on an anion exchange resin at a high efficiency, and that the adsorbed heavy metal ions and chlorine ions are desorbed by elution with water.

EXAMPLE 7

Copper bromide, zinc bromide and 47% hydrobromic acid were dissolved in a mixture of acetic acid and 7% of water to prepare as a starting solution an acetic acid solution having concentrations of metal ions and bromine ions as indicated in Table 8, and 30 liters of the so prepared acetic acid solution were passed at a rate of 2 liters/hour through a column packed with 3 liters of an anion exchange resin in which 75% of the ion-exchange groups was in the bromide state and which had been prepared in the same manner as described in Example 5 by using the anion exchange resin in the bromide state as prepared in Example 1. The effluent had concentrations of metal ions and bromine ions as shown in Table 8. Then, 5 liters of a 2 N aqueous solution of sulfuric acid were passed at a rate of 2 liters/hour through the column to obtain an eluate having concentrations of metal ions and bromine ions as shown in Table 8.

TABLE 8

| | Ion Concentrations (ppm) | | |
|---|---|---|---|
| | Cu | Zn | Br⁻ |
| Starting Solution | 24 | 31 | 1250 |
| Effluent | <1 | <1 | 110 |
| Eluate | 143 | 185 | 6830 |

EXAMPLE 8

A titanium pressure-resistant reaction vessel (internal capacity: 40 liters) equipped with a stirrer, a baffle plate, a thermometer, a heating jacket and a reflux condenser was charged with 20 kg of acetic acid (purity: 99.5%), 20 g as metallic cobalt of cobalt (II) bromide (hexahydrate) and 20 g as metallic manganese of manganese (II) acetate (tetrahydrate). Under such reaction conditions that the temperature was 200° C. and the pressure was 20 kg/cm²·G, an acetic acid solution containing 10% of p-xylene in a solution of the same composition as charged in the vessel was continuously introduced into the reaction vessel at a rate of 20 kg/hr for 5 hours while simultaneously introducing air into the vessel at a rate of 5 kg/hr. During the reaction, the reaction mixture was continuously withdrawn from the reaction vessel into a crystallizing tank made of a stainless steel SUS-316L, in which the temperature and the pressure was respectively maintained at 180° C. and at 10 kg/cm²·G. After completion of the reaction, the reaction mixture in the crystallizing tank was subjected to solid-liquid separation to obtain terephthalic acid crystals and a mother liquor having a water concentration of 5%.

On the other hand, an anion exchange resin Dowex 1×4 (particle size=100−200 mesh) was contacted with an acetic acid solution containing 4% of 47% hydrobromic acid and then washed with a mixture of acetic acid and water (water content: 50%) in an amount 5 times by volume as large as the resin. A glass column having an internal diameter of 30 mm and a height of 1,800 mm and equipped with a jacket was packed with the so treated anion exchange resin to a height of 1,500 mm.

While maintaining the column temperature at 85° C., 18 liters of the above-mentioned mother liquor having concentrations of metal ions and bromine values as indicated in Table 9 were passed through the column at a rate of 2 liters/hr to obtain an effluent having concentrations of metal ions and bromine values as shown in Table 9. No substantial presence of cobalt ions was detected in the effluent. Then, 2.5 liters of water were passed through the column at a rate of 2 liters/hr to obtain an eluate having concentrations of metal ions and bromine values as shown in Table 9.

TABLE 9

|  | Concentration (ppm) | | | | | | |
|---|---|---|---|---|---|---|---|
|  | Co | Mn | Fe | Cr | Ni | Br⁻ | Br° |
| Mother Liquor | 750 | 700 | 52 | 13 | 15 | 620 | 1800 |
| Effluent | <1 | 72 | 46 | 12 | 13 | 35 | 1620 |
| Eluate | 5400 | 4520 | 43 | 6 | 14 | 5510 | 210 |

Note.
Br⁻: bromine ion
Br°: bromine in the form of non-dissociative bromine compounds (In the subsequent Examples, the bromine ion and the bromine in the form of non-dissociative bromine compounds will be symolized in the same manner.)

The concentration of the bromine in the form of non-dissociative bromine compounds was calculated by subtracting the bromine ion concentration from the total bromine concentration.

EXAMPLE 9

Anion exchange resins Dowex II×8 and 21K, Amberlite IRA-68 and IRA-402, Dia Ion 316 and Ionac A-580, and a vinylpyridine type anion exchange resin (gel type: cross-linking degree=20) treated in the same manner as described in Example 8 were respectively packed in a seven columns having an internal diameter of 30 mm and a height of 1,800 mm and equipped with a jacket to a height of 1,500 mm. While maintaining the column temperature at 85° C., 25 liters of the same mother liquor as obtained in Example 8 were passed at a rate of 2 liters/hr through each column to obtain an effluent having concentrations of metal ions and bromine values as shown in Table 10.

TABLE 10

| Run No. | Anion Exchange Resin | | Concentration (ppm) in Effluent | | | | | | |
|---|---|---|---|---|---|---|---|---|---|
|  | Kind | Particle Size (mesh) | Co | Mn | Fe | Cr | Ni | Br⁻ | Br° |
| 1 | Dowex II × 8 | 50-100 | 250 | 310 | 50 | 12 | 14 | 55 | 1520 |
| 2 | Dowex 21K | 20-50 | 83 | 260 | 49 | 11 | 14 | 43 | 1260 |
| 3 | IRA-68 | 20-50 | 320 | 420 | 49 | 10 | 13 | 42 | 1680 |
| 4 | Dia Ion 316 | 20-50 | 48 | 210 | 50 | 11 | 13 | 31 | 1310 |
| 5 | IRA-402 | 20-50 | 162 | 250 | 49 | 11 | 12 | 36 | 1320 |
| 6 | Ionac A-580 | about 30 | 54 | 165 | 49 | 11 | 11 | 48 | 1350 |
| 7 | Vinyl-pyridine type | 50-100 | 20 | 30 | 48 | 12 | 10 | 12 | 1250 |

Then, 18 liters of a mixture of acetic acid and 25% of water were passed through each column to desorb and recover cobalt, manganese and bromine ions. the concentrations of metal ions and bromine values in the eluate are shown in Table 11 in which Run Nos. correspond to those in Table 10.

TABLE 11

| Run No. | Concentration (ppm) in Eluate | | | | | | |
|---|---|---|---|---|---|---|---|
|  | Co | Mn | Fe | Cr | Ni | Br⁻ | Br° |
| 1 | 545 | 389 | 2 | 1 | 1 | 560 | 120 |
| 2 | 663 | 430 | 2 | 2 | 1 | 580 | 105 |
| 3 | 420 | 270 | 2 | 3 | 1 | 530 | 130 |
| 4 | 701 | 490 | 2 | 2 | 1 | 602 | 125 |
| 5 | 585 | 438 | 3 | 2 | 2 | 583 | 160 |
| 6 | 695 | 531 | 3 | 2 | 3 | 572 | 185 |
| 7 | 728 | 655 | 4 | 1 | 1 | 605 | 130 |

As will be apparent from the results as shown in Table 10 and 11, the recovery of cobalt, manganese and bromine ions and the removal of iron, chromium and nickel ions can be accomplished by the use of any of tertiary amine type anion exchange resins (Run Nos. 3 and 4), quaternary ammonium type anion exchange resins (Run Nos. 1, 2, 5 and 6) and vinyl pyridine type anion exchange resins (Runs Nos. 6 and 7), and cobalt, manganese and bromine ions can be desorbed and recovered by elution with a mixture of acetic acid and water.

EXAMPLE 10

In the same manner as described in Example 8, the same mother liquor as obtained in Example 8 was contacted with the same anion exchange resin as used in Example 8, to obtain 100 liters of an effluent. The effluent was introduced at a rate of 8 kg/hr into a distillation column made of a stainless steel SUS-316L and packed with Rasching rings and distillation was carried out at a column top temperature of 114° C. A mixture of acetic acid and water was distilled off from the column top and 1 kg of the concentrate containing non-dissociative bromine compounds was recovered from the column bottom. The concentrate was passed at a rate of 1 kg/hr through an Arthur-Smith thin film distillation column having a rotary ring and a cooling zone in the interior thereof to separate the concentrate into a high boiling point component and a low boiling point component. Data of the contents of iron, chromium and nickel ions and non-dissociative bromine compounds in the low boiling point component are shown in Table 12, in relation with the cylinder temperature and the pressure.

TABLE 12

| | Operation Conditions | | Low Boiling Point Component | | |
|---|---|---|---|---|---|
| Run No. | Cylinder Temperature (°C.) | Pressure (mm Hg abs.) | Iron, Chromium and Nickel Ions (g)* | Br° (g) | Br° Recovery (wt %) |
| 1 | 70 | 30 | <0.001 | 1.36 | 18 |
| 2 | 125 | 30 | <0.001 | 3.55 | 47 |
| 3 | 160 | 30 | <0.001 | 5.14 | 68 |
| 4 | 190 | 30 | <0.001 | 5.34 | 71 |
| 5 | 45 | 6.5 | <0.001 | 1.59 | 21 |
| 6 | 88 | 6.5 | <0.001 | 3.40 | 45 |
| 7 | 115 | 6.5 | <0.001 | 6.73 | 89 |
| 8 | 155 | 6.5 | <0.001 | 6.58 | 87 |
| 9 | 50 | 1 | <0.001 | 4.61 | 61 |
| 10 | 80 | 1 | <0.001 | 5.90 | 78 |
| 11 | 100 | 1 | <0.001 | 6.96 | 92 |
| 12 | 147 | 1 | <0.001 | 6.96 | 92 |

*the sum of amounts of iron, chromium and nickel ions

EXAMPLE 11

In a 5-tray type distillation column, the same concentrate as used in Example 10 was fed into the third tray from the column top and distillation was carried out at a reflux ratio of 0.7 under operation conditions as shown in Table 13 to separate the concentrate into a low boiling point component and a high boiling point component. Data of the contents of iron, chromium and nickel ions and non-dissociative bromine compounds in the low boiling point component are shown in Table 13, in relation with the vapor temperature and the pressure.

TABLE 13

| | Operation Conditions | | Low Boiling Point Component | | |
|---|---|---|---|---|---|
| Run No. | Vapor Temperature (°C.) | Pressure (mm Hg abs.) | Iron, Chromium and Nickel Ions* (g) | Br° (g) | Br° Recovery (wt %) |
| 1 | 62 | 15 | <0.001 | 3.33 | 37 |
| 2 | 87 | 15 | <0.001 | 5.58 | 62 |
| 3 | 130 | 15 | <0.001 | 7.83 | 87 |
| 4 | 168 | 15 | <0.001 | 8.37 | 93 |
| 5 | 90 | 80 | <0.001 | 3.78 | 42 |
| 6 | 120 | 80 | <0.001 | 7.29 | 81 |
| 7 | 160 | 80 | <0.001 | 7.83 | 87 |

Note
*the sum of amounts of iron, chromium and nickel ions

EXAMPLE 12

An anion exchange resin Dowex 1×4 (particle size=200—400 mesh) was converted into an anion exchange resin in the hydroxide state in the same manner as described in Example 1, and 1 liter of the so converted resin was packed in a column having an internal diameter of 4 cm and equipped with a jacket. The column temperature was maintained at 90° C. Then, 10 liters of the same effluent as obtained in Example 8 were passed as the starting solution through the column at a space velocity of 3 hr$^{-1}$ and the resulting effluent was analyzed. Then, 2 liters of a 5% aqueous solution of sodium hydroxide were passed through the column at a space velocity of 2 hr$^{-1}$ to recover the adsorbed bromine ions. The obtained results are shown in Table 14.

TABLE 14

| | Concentration (ppm) | | | | | | |
|---|---|---|---|---|---|---|---|
| | Co | Mn | Fe | Cr | Ni | Br$^-$ | Br° |
| Starting solution | <1 | 72 | 46 | 12 | 13 | 35 | 1620 |
| Effluent | <1 | 13 | 32 | 3 | 4 | <1 | 11 |
| Eluate | <1 | 293 | 68 | 45 | 43 | 8200 | 120 |

What is claimed is:

1. A process for recovering heavy metal ions and organic bromine compounds from a mother liquor of a reaction mixture derived from liquid phase oxidation to a carboxylic acid of a substituted benzene oxidizable thereto by means of a molecular oxygen-containing gas in a lower aliphatic monocarboxylic acid in the presence of a heavy metal catalyst system and a bromine compound as a reaction promotor, which comprises the step of contacting said mother liquor comprising a lower aliphatic monocarboxylic acid, water in an amount less than 20% by weight and heavy metal ions, dissolved therein, of at least one member selected from the group consisting of vanadium, cobalt, chromium, manganese, nickel, copper, zinc, molybdenum and iron and halogen values in the form of bromine ions, non-dissociative bromine compounds and organic bromine compounds, with an anion exchange resin, at least 60% of the ion-exchange groups of said anion exchange resin being in the bromide state, thereby adsorbing said heavy metal ions and bromine ions on the anion exchange resin to remove the same from the mother liquor; and the steps of subjecting the resulting mother liquor to a distillation comprising a first step distillation to recover the lower aliphatic monocarboxylic acid and a second step distillation which is carried out so that the relationship between the vapor temperature and the distillation pressure satisfies the requirement represented by the following equation:

$$\log p \leqq 9.57 - \frac{3330}{t + 348}$$

wherein p stands for the distillation pressure (mmHg absolute) and t stands for the vapor temperature (°C.), to recover the remaining non-dissociative and organic bromine compounds which had not been adsorbed in the preceding step.

2. A process according to claim 1, wherein said substituted benzene has 1 to 4 substituents selected from the group consisting of $C_1$–$C_3$ alkyl, aldehyde and carboxyl, and when said substituted benzene has a carboxyl group, it further has at least one substituent other than carboxyl.

3. A process according to claim 1, wherein said substituted benzene is p-xylene and said lower aliphatic monocarboxylic acid is acetic acid.

4. A process according to claim 1, wherein said mother liquor of reaction mixture is contacted with said anion exchange resin at a temperature of 30° to 120° C.

5. A process according to claim 1, wherein said mother liquor of reaction mixture is contacted with said anion exchange resin at a temperature of 50° to 100° C.

6. A process according to claim 1, wherein said heavy metal ions are at least one ion selected from the group consisting of cobalt and manganese ions.

7. A process according to claim 1, wherein said second step distillation is carried out by using a rotary thin layer evaporator.

* * * * *